United States Patent [19]

Enger

[11] 4,177,800

[45] Dec. 11, 1979

[54] IMPLANTABLE BIOTELEMETRY TRANSMITTER AND METHOD OF USING SAME

[76] Inventor: Carl C. Enger, 12700 Lake Ave., Lakewood, Ohio 44107

[21] Appl. No.: 894,811

[22] Filed: Apr. 10, 1978

[51] Int. Cl.$^2$ .............................................. A61B 5/00
[52] U.S. Cl. ............................ 128/2.1 A; 128/419 B
[58] Field of Search ............... 128/2.1 A, 2.05 P, 2 P, 128/419 B, 419 E

[56] References Cited

U.S. PATENT DOCUMENTS

| | | | |
|---|---|---|---|
| 3,407,363 | 10/1968 | Kaiser et al. | 128/419 B |
| 3,456,134 | 7/1969 | Ko | 128/419 B |
| 3,682,160 | 8/1972 | Murata | 128/2 P |
| 3,971,362 | 7/1976 | Pope et al. | 128/2.1 A |

*Primary Examiner*—William E. Kamm
*Attorney, Agent, or Firm*—Browdy and Neimark

[57] ABSTRACT

An implantable device for monitoring heart action or action of any other periodic-moving living organ or part of a living body. The device includes a piezoelectric energy converter which is driven by the adjacent moving tissue and which thereby generates electrical energy. The device also includes a pulse generator which in turn keys a radio transmitter circuit. The transmitter circuit is modulated during "on" periods by a signal from the organ being monitored, for example, an EKG signal from the patient's heart. The components are energized solely from the piezo-generated electrical energy. The rate and duration of the keyed bursts of modulated radio transmission depend on the amount of electrical power furnished by the converter. A method of using the device to monitor action of an organ such as the heart of a living body includes implanting the device, powering it from a pulsating portion of the body producing short, spaced r.f. bursts and modulating the bursts with signals representative of data from the heart.

9 Claims, 2 Drawing Figures

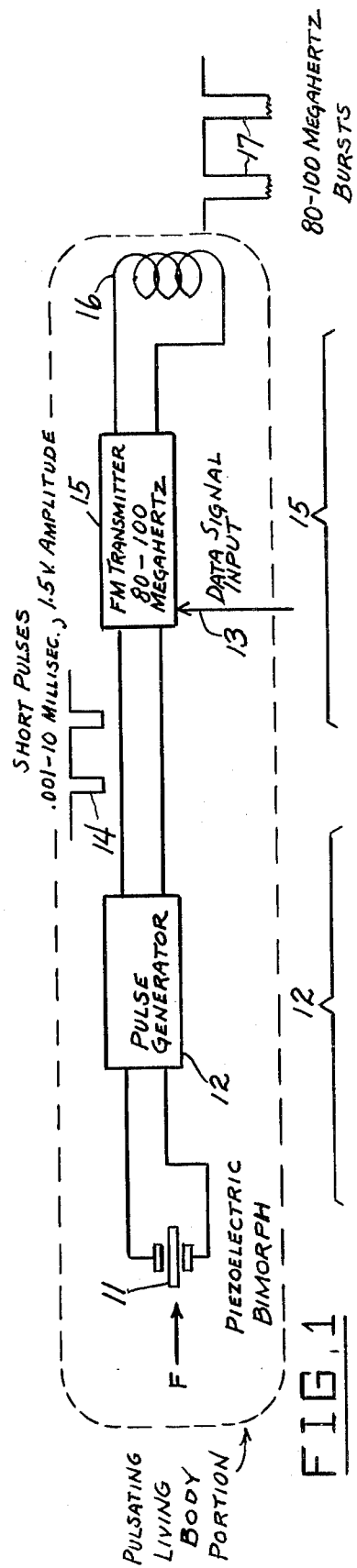
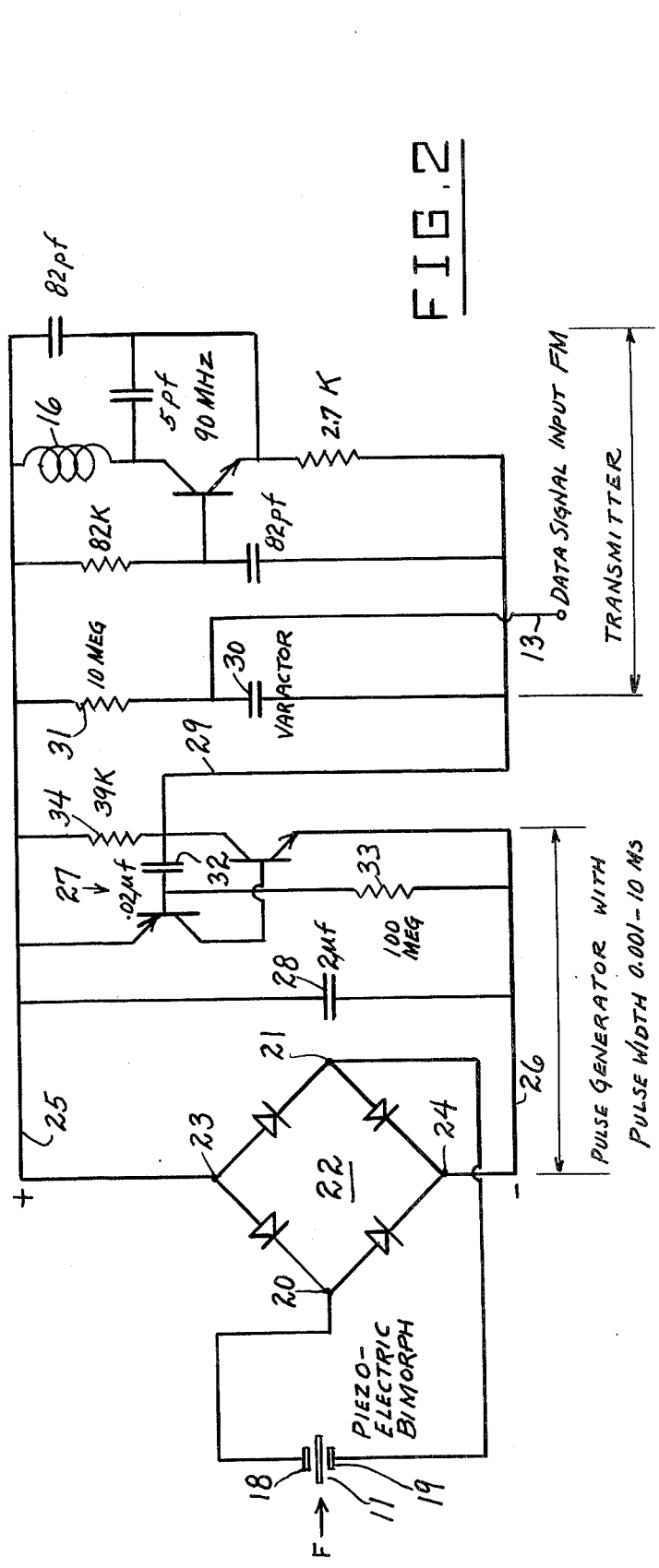

IMPLANTABLE BIOTELEMETRY TRANSMITTER AND METHOD OF USING SAME

FIELD OF THE INVENTION

This invention relates to implantable telemetry devices for monitoring portions of living bodies, and more particularly to remote-monitoring self-powered devices providing keyed bursts of radio frequency energy modulated by signals produced by the organs under study.

BACKGROUND OF THE INVENTION

Remote monitoring of heart action, or the action of other living organs has been heretofore performed by the use of implanted radio transmitters, usually energized by mercury cells or other chemical battery supply means. The operating life of such an implanted transmitter is limited by the relatively short operational life of the associated battery, as in the case of currently employed heart pacemaker apparatus.

Known radio telemetry systems of the self-powered type, such as that disclosed, for example, in U.S. Pat. No. 4,001,798 to Roland L. Robinson, are intended to provide continuous radio transmission energized by a transducer, the transducer serving both as a power generating means to drive the associated radio transmitter and as a means to modulate the transmitter, whereby to transmit the transduced signal. Since a considerable amount of power output is required from the transducer, for example, a piezoelectric crystal slab, said transducer must be relatively large and bulky. Although this presents no serious problems for industrial applications wherein there is usually ample space for the transducer and associated radio transmitting apparatus, it is not practical for biotelemetry systems where the apparatus is required to be implanted in a living body.

Previously used implantable biotelemetry transmitters (employing batteries, or the like, as power sources) are either continuously energized or turned on and off with a magnetic reed switch which can be activated from outside the body. All of the previously used approaches dictate short power supply life. There is a need for the usage in these systems of a biological energy converter wherein there is no depletion of a discrete quantity of power as occurs with a mercury cell or a nuclear reactor type of power supply.

SUMMARY OF THE INVENTION

Accordingly, an object of the present invention is to overcome deficiencies in the prior art, such as indicated above. Another object is to provide an improved implantable radio telemetry system which overcomes the deficiencies of the previously employed systems.

A further important object of the invention is to provide a novel and improved implantable radio telemetering system which can relay biological data from within the body to exterior receivers without the need for chemical power supplies. An additional object of the invention is to provide a method of monitoring action of an organ of a living body using the implantable transmitter of the invention.

A still further object of the invention is to provide an improved implantable radio telemetry transmitter which is selfpowered and which does not suffer depletion of a discrete quantity of power such as occurs with mercury cells or other types of chemical power sources.

A still further object of the invention is to provide an improved implantable radio telemetry transmitter which can be used with a heart pacemaker to monitor physiologic action or to monitor the character of a pacemaker's output, and which employs a piezoelectric element which can be used to energize both the pacemaker circuitry and the radio transmitter.

A still further object of the invention is to provide an improved implantable radio telemetry transmitter energized from an implanted piezoelectric element and wherein the transmitter is modulated by a signal providing data from an associated organ being monitored, and wherein the transmitter is repeatedly switched off for periods of time to conserve available energy, forming output pulses modulated by the superimposed data from the monitored organ, thus enabling a relatively small piezoelectric element to be employed.

A still further object of the invention is to provide an improved radio telemetry transmitter which can be used to monitor physiologic response to the administration of drugs at various points in the body.

DESCRIPTION OF A PREFERRED EMBODIMENT

Referring to the drawings, FIG. 1 is a block diagram of an implantable biotelemetry device which can be suitably implanted in a living body in physical engagement with an organ to be monitored, for example, the heart muscle, and the biotelemetry system can be used in conjunction with a pacemaker. This biotelemetry system can also be used to monitor physiologic responses at points remote from the energizing source. The implantable telemetry unit is provided with a piezoelectric power transducer 11, which may comprise a piezoelectric bimorph arranged to be stressed by the heart muscle, or other organ to be monitored, and can be used, in the case of the heart muscle, to energize both the associated pacemaker circuitry and the herein-disclosed monitoring telemetry radio transmitter. The present disclosure is concerned only with the monitoring telemetry radio transmitter.

The electrical output of the piezoelectric transducer 11 is furnished to a pulse generator 12, providing short bursts of an associated transmitter 15 which may be modulated by an appropriate signal input, for example, an EKG signal input, as is diagrammatically shown at 13. The signal input at 13 is obtained in a conventional manner, as by the use of suitable electrodes or sensors.

The pulse output of the pulse generator 12 is in the form of short pulses 14, for example, of 0.001–10 millisecond duration, depending on the nature of the data to be transmitted, and may be of about 1.5 v. average amplitude. This pulse output is employed to key and drive an FM radio transmitter 15 having a tank circuit oscillator coil 16 which may be employed as an antenna. The output of the FM radio transmitter 15 is in the form of frequency-modulated 80–100 megahertz bursts of radio frequency emission. The transducer 11 acts as the circuit energizing device, and the available energy is in accordance with the amplitude and frequency of variations of pressure on the crystal.

Referring to FIG. 2, the respective transducer electrodes 18,19 are connected to the input terminals 20,21 of a conventional bridge rectifier 22, and the output terminals 23,24 of said rectifier are connected to the respective positive and negative output wires 25 and 26. A conventional pulse-generating circuit 27 is energized from the wires 25,26, across which a relatively largecapacity voltage-smoothing storage capacitor 28 is connected.

The pulse-generating circuit 27 acts to switch power to its output wire 29 at a predetermined rate and for predetermined lengths of time, depending upon the nature of the data to be transmitted. The available power is limited by the electrical power-generating capability of the piezoelectric element unit 11. By narrowing the pulse length of the supply voltage at 29, more transmitter RF bursts can be obtained within each pulse period, within the limits of the energy-generating capability of said element unit 11.

The carrier frequency of transmitter 15 can be set at any desired point in the spectrum. Relatively high carrier frequencies are preferred because this reduces the bulk of the components of the apparatus and facilitates implantation. In the typical embodiment herein disclosed, the transmitter 15 has a nominal carrier frequency of 90 MHz and is frequency-modulated between 80-100 MHz by the modulation signal at 13, which is furnished to the junction of an input shunt circuit resistor 31 and a Varactor 30, defining a circuit to modulate the frequency of transmitter 15 around said carrier frequency in accordance with the input data.

As above mentioned, the transmitter 15 is switched entirely off for periods of time (between bursts) which can be varied, by suitable component changes, in accordance with the available energy. The transmitter energy-control pulses at 29 can be narrowed and spaced closer together in order to add definition to the transmission of data.

The output signal from transmitter 15 may be received by conventional FM receiving and decoding apparatus and suitably converted for visual or other desired readout.

The pulse frequency and duty cycle of the pulse generator 12 may be changed, as desired, by suitably changing the values of the capacitor 32 and the resistors 33,34 associated therewith.

It will be noted that within the spirit of the present invention, the above-described telemetry device may be implanted to capture mechanical forces from any part of the living body, for example, in any pulsating portion or organ of the body, such as the lungs or regions adjacent thereto, heart muscle, or the like.

The invention, in its method aspect, is a method of monitoring the action of at least one organ of a living body without requiring the use of chemical power supply means. This includes providing a transmitter including transducer means adapted to be mechanically moved by a pulsating portion of the living body to provide electrical power output, pulse forming means coupled to transducer means and responsive to its electrical power output for producing short pulses of predetermined width and repetition rate, radio transmitting means coupled to the pulse-forming means and responsive to the short pulses for generating successive spaced radio frequency carrier bursts of substantially predetermined width, with separate modulation means adapted to respond to a signal representing at least one body function for independently modulating the transmitting means. The method involves implanting the transmitter with its transducer means positioned to be moved by the pulsating portion of the living body. The modulation means is responsive to a signal derived from and representing the at least one body function. Short modulated radio frequency output busts are produced from the transmitter, data representing the action of the at least one organ being carried as modulation of the bursts.

While a specific embodiment of an improved biotelemetry method and apparatus has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. A telemetry transmitter adapted to be implanted in a living body, the transmitter comprising transducer means adapted to be mechanically moved by a pulsating portion of the living body to provide electrical power output; pulse-generating means coupled to said transducer means and responsive to its electrical power output for producing short pulses of predetermined width; radio transmitting means coupled to said pulse-generating means and responsive to the short pulses for generating successive spaced radio carrier frequency signal bursts of substantially said predetermined width and modulation means adapted to respond to a signal representing at least one body function for independently modulating said transmitting means, whereby the transmitter transmits during ON times determined by the given width of the pulses and the bursts carry modulation representing the at least one body function.

2. The telemetry transmitter of claim 1, wherein said pulse-generating means includes means to derive a d.c. voltage at the output of said transducer means for providing power of said pulse-generating means.

3. The telemetry transmitter of claim 2, including said pulse-generating means includes circuit means connecting the output thereof to said transmitting means for alternately turning said transmitting means ON or OFF responsive to the pulses formed by said pulse-generating means, the transmitting means generating successive spaced short radio frequency bursts constituting the signal bursts.

4. The telemetry transmitter of claim 3, wherein said modulation means comprises circuit means connected to said transmitting means to vary the frequency of the radio frequency short bursts around a nominal frequency in accordance with signal data.

5. The telemetry transmitter of claim 1, wherein said transducer means comprises a piezoelectric energy converter.

6. The telemetry transmitter of claim 5 wherein said pulse-generating means includes a bridge rectifier, to output terminals of said transducer means, and storage filter means connected across output terminals of said bridge rectifier to derive a substantially steady d.c. voltage providing power of said pulse-generating means.

7. The telemetry transmitter of claim 1, wherein said modulation means comprise means for varying the radio frequency of said transmitting means.

8. The telemetry transmitter of claim 1, wherein said transmitter means comprises transmitter means which produce a carrier frequency of approximately 90 megahertz.

9. The telemetry transmitter of claim 1, wherein said modulation means comprises means for varying the carrier frequency about approximately 90 megahertz in accordance with the signal representing the body function.

* * * * *